US010517989B1

(12) United States Patent
Arnold (10) Patent No.: US 10,517,989 B1
(45) Date of Patent: Dec. 31, 2019

(54) ENHANCED MEDICAL DRESSING APPARATUS, SYSTEM, AND METHOD (71) Applicant: Jonathan F. Arnold, Burlington, IA (US)

(72) Inventor: Jonathan F. Arnold, Burlington, IA (US)

(*) Notice: Subject to any disclaimer, the term of this patent is extended or adjusted under 35 U.S.C. 154(b) by 118 days.

(21) Appl. No.: 15/821,642

(22) Filed: Nov. 22, 2017

Related U.S. Application Data (60) Provisional application No. 62/426,208, filed on Nov. 23, 2016.

(51) Int. Cl.
A61L 15/32 (2006.01)
A61L 26/00 (2006.01)
A61K 31/5377 (2006.01)

(52) U.S. Cl.
CPC ...... *A61L 26/0033* (2013.01); *A61K 31/5377* (2013.01); *A61L 15/325* (2013.01); *A61L 26/0023* (2013.01); *A61L 26/0066* (2013.01); *A61L 26/0085* (2013.01); *A61L 2300/406* (2013.01); *A61L 2420/02* (2013.01)

(58) Field of Classification Search
CPC .............. A61L 15/325; A61L 26/0033; A61L 2300/406; A61L 2420/02
See application file for complete search history.

(56) References Cited

U.S. PATENT DOCUMENTS

| 5,790,256 | A | 8/1998 | Brown et al. |
| 6,331,893 | B1 | 12/2001 | Brown et al. |
| 7,833,790 | B2* | 11/2010 | Cullen ............... A61L 15/225 435/423 |
| 7,926,363 | B2 | 4/2011 | Miller et al. |
| 8,109,014 | B2 | 2/2012 | Miller et al. |
| 8,170,705 | B2 | 5/2012 | Koelling et al. |
| 8,613,716 | B2 | 12/2013 | Summit et al. |
| 8,728,498 | B2 | 5/2014 | Zhang et al. |
| 8,784,898 | B2 | 7/2014 | Archambeau et al. |
| 8,838,263 | B2 | 9/2014 | Sivak et al. |
| 9,020,626 | B2 | 4/2015 | Spector |
| 9,095,569 | B2 | 8/2015 | Shoseyov et al. |
| 9,174,839 | B2 | 11/2015 | Abbott et al. |
| 9,364,331 | B2 | 6/2016 | Wasielewski |
| 2006/0070260 | A1 | 4/2006 | Cavanagh et al. |
| 2006/0172000 | A1 | 8/2006 | Cullen et al. |

(Continued)

FOREIGN PATENT DOCUMENTS

WO 2015199699 A1 12/2015

*Primary Examiner* — Theodore R. West (74) *Attorney, Agent, or Firm* — John Rizvi; John Rizvi, P.A.—The Patent Professor®

(57) ABSTRACT

An enhanced medical dressing for treatment of wounds is provided. A dressing is augmented by one or more enhancers thereon. The enhancers include a collagen, an antibiotic, or both. The enhanced medical dressing is prepared by placing and mixing the collagen, the antibiotic, and the dressing within a container. On mixing, the enhanced medical dressing is formed such that the enhancer adheres to the dressing by, for example, adsorption or an electrostatic force. The enhanced medical dressing when applied to the wound causes the collagen and the antibiotic to be released into the wound. Further, the enhanced medical dressing degrades over time due to contact with physiological moisture.

13 Claims, 11 Drawing Sheets (56) References Cited

U.S. PATENT DOCUMENTS

| | | |
|---|---|---|
| 2010/0047324 A1 | 2/2010 | Fritz et al. |
| 2012/0191026 A1 | 7/2012 | Aali et al. |
| 2013/0017227 A1 | 1/2013 | Lambert, Jr. et al. |
| 2014/0276235 A1 | 9/2014 | Raniere |
| 2014/0341866 A1* | 11/2014 | Huang .................... A61L 27/26 424/93.7 |
| 2016/0106878 A1 | 4/2016 | Yang et al. |
| 2016/0235158 A1 | 8/2016 | DesJardins et al. |

* cited by examiner

ENHANCED MEDICAL DRESSING APPARATUS, SYSTEM, AND METHOD

CROSS-REFERENCE TO RELATED APPLICATION

This application claims the benefit of U.S. Provisional Patent Application Ser. No. 62/426,208, filed Nov. 23, 2016, which is incorporated herein in its entirety.

FIELD OF THE INVENTION

The present invention relates generally to enhanced medical dressings, and more particularly, to an enhanced medical dressing system and method for treating wounds.

BACKGROUND OF THE INVENTION

An enhanced medical dressing may be a sterile pad or compress that is appliable to a wound to promote healing of the wound and protect the wound from further harm. For example, an enhanced medical dressing is usually designed to be in direct contact with a wound. Dressings may be specifically designed and applied to provide a sterile, breathable, and moist environment that may reduce a risk of infection, help a wound heal more quickly, and reduce scarring.

Microorganisms may grow in extracellular polymeric aggregates known as biofilms. For example, bacterial biofilms may grow in or around a skin wound or infection. Normally, acute infections are treatable with antibiotics. But, bacteria of a wound may succeed in forming a biofilm, and subsequently the wound may become untreatable and may develop into a chronic state, since chronic biofilm-based infections may have an extreme resistance to antibiotics or other conventional antimicrobial agents, and have an extreme capacity for evading host defenses. Bacteria may use quorum sensing to coordinate biofilm formation, virulence, and antibiotic resistance.

Antibiotics, such as topical linezolid, are needed to combat antibiotic resistant infections. There is emerging evidence that linezolid inhibits bacterial quorum sensing, and therefore may be beneficial in treating established biofilms. In addition, topical antibiotic preparations assist in decreasing the formation of wound biofilm and promoting autolytic debridement. However, such antibiotics are currently available only in oral and intravenous preparations.

Accordingly, there is an established need for an enhanced medical dressing and method that interferes with quorum sensing and thus promotes wound healing.

SUMMARY OF THE INVENTION

Disclosed is a method of preparing an enhanced medical dressing for treating a wound, the method comprising augmenting a dressing with an enhancer to form an enhanced dressing.

In another aspect, the dressing is an enhanced medical dressing for treating flesh wounds.

In another aspect, the enhancer is a composition including at least one of collagen and an antibiotic.

In another aspect, the collagen is a collagen powder and the antibiotic is linezolid.

In another aspect, the antibiotic is in the form of a powder.

In another aspect, the collagen is in the form of a liquid.

In another aspect, the collagen is in the form of a gel.

In another aspect, the antibiotic is in the form of a liquid.

In another aspect, the antibiotic is in the form of a gel.

In another aspect, in the augmenting step, at least one of the dressing and the enhancer is configured to cause the dressing and the enhancer to adhere to one another.

In another aspect, the dressing and the enhancer are configured to adhere to one another via electrostatic force.

In another aspect, the augmenting step includes mixing the dressing and the enhancer in a container.

In another aspect, the dressing is configured to degrade in contact with physiological moisture.

In another aspect, the dressing is a collagen dressing including oxidized regenerated cellulose and collagen.

In another aspect, at least one of the collagen and antibiotic are configured to be released into a wound contacting the enhanced dressing.

In another aspect, the method further comprises, fragmenting the dressing to increase a surface area of the dressing.

In another aspect, the dressing and the enhancer are provided in a kit.

In another aspect, the method further comprises, applying the enhanced dressing to a wound.

Furthermore, disclosed is an apparatus for treating a wound, the apparatus comprising a material including collagen and an antibiotic, the material configured to degrade in contact with physiological moisture to release collagen, and the antibiotic from the material.

In another aspect, the material is fragmented to increase a surface area of the material.

Also disclosed is a system for treating a wound, the system comprising a material including collagen, a collagen enhancer, and an antibiotic enhancer, wherein the material, the collagen enhancer, and the antibiotic enhancer, are configured to attach to one another upon being mixed together in a container.

In another aspect, the material is an absorbent, open-pored, sterile, matrix including collagen and oxidized regenerated cellulose.

In another aspect, the enhanced medical dressing is modular, so that any two of three components may be combined to exceed the function of a single component.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
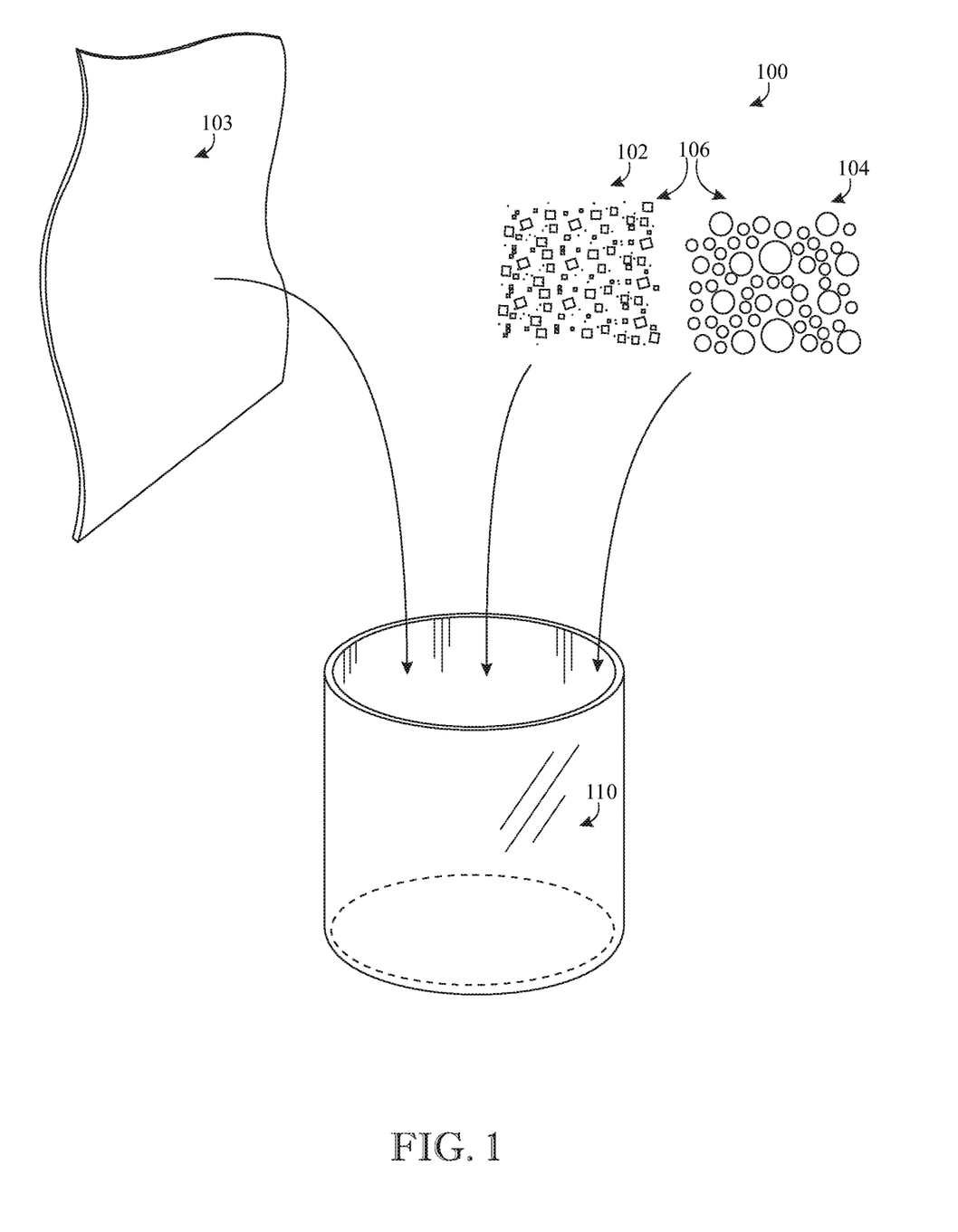
FIG. 1 schematically presents elements required for preparing an enhanced medical dressing, the elements being placed into a container, in accordance with aspects of the present disclosure.

Referring to FIG. 1, an exemplary set-up 100 (e.g., a group of elements) for preparing an enhanced medical dressing is illustrated. The set-up 100 includes a number of elements, materials, structures, or substances that can be used to prepare an enhanced medical dressing for treating wounds.

Figure 6:
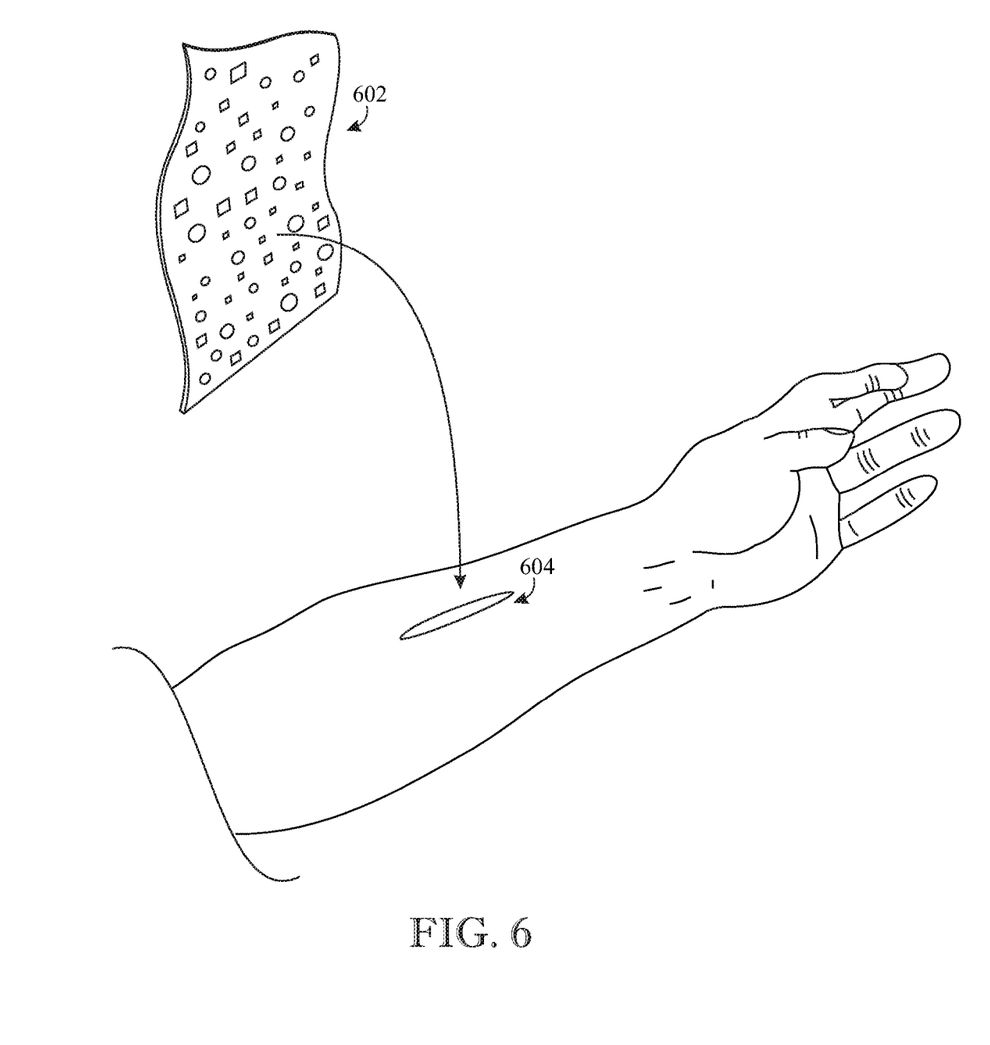
FIG. 6 presents a perspective view of applying the enhanced medical dressing for treating a wound, in accordance with aspects of the present disclosure.

The set-up 100 and its various substances and/or materials may be provided to a user in or as a kit. Such a kit may contain a dressing 103 and one or more enhancers 106. The kit may include the enhancers 106 and a container 110 for mixing the enhancers 106 with the dressing 103 in the container 110 as shown in FIG. 1. In some embodiments, the kit may include the enhancers 106 excluding the container 110. In FIG. 1, two enhancers 106 are shown (e.g. including first enhancer 102 and second enhancer 104). The enhancers 106 may be or may include a collagen enhancer 102 and an antibiotic enhancer 104 respectively. The kit may include the dressing 103 and the collagen enhancer 102, excluding the antibiotic enhancer 104. In other embodiments, the kit may include the dressing 103 and the antibiotic enhancer 104, excluding the collagen enhancer 102. As shown in FIG. 1, the dressing 103, the collagen enhancer 102, and the antibiotic enhancer 104 may be combined in a container 110 to produce an enhanced medical dressing 602 (FIG. 6). Further, FIG. 6 shows enhanced medical dressing 602 being applied to a wound 604.

Turning back to FIG. 1, the set-up 100 may be transported such that the dressing 103, the collagen enhancer 102, and the antibiotic enhancer 104 are individually packaged or wrapped in a suitable material to avoid intermixing the substances until preparing the enhanced medical dressing 602 is required. When preparing the enhanced medical dressing 602 is required, the dressing 103, the collagen enhancer 102, and the antibiotic enhancer 104 may be removed from their individual packaging to begin preparing the enhanced medical dressing 602.

In one embodiment, a quantity of the substances in the kit may be appropriately proportioned so that the kit is in a ready to use form for treatment of specific flesh wounds. The proportion of the substances may be decided based on a size of the wound and/or a severity of the wound such that the kit may be used for a one-time application by a user. Texture, particle size, and relative proportion of the substances with respect to each other and the size of the dressing 103 may vary based on application requirements.

Standard dosing of the herein disclosed substances may vary or be appropriately selected. For example, the dressing 103 (e.g. collagen, collagen-ORC, or collagen-ORC-silver dressing) may have a typical dimension of 3 $cm^2$ and may be resized to fit most wounds. The dressing may be stacked in layers to fill deeper wounds. The dressing may be cut to address areas of tunneling and/or undermining. The antibiotic (linezolid, tedizolid, ciprofloxacin, metronidazole, rifampin) may have a mass of 200-250 mg. The collagen powder may have a mass of 200 mg. The amount of antibiotic and hydrolyzed collagen powder may be adjusted proportionally with respect to a size of the dressing. The enhanced dressing may be applied daily, every other day, three days a week (Monday, Wednesday, Friday), every 7-10 days, more than once daily, or as needed to maintain a moisture-balanced wound healing environment. Antibiotics may be combined empirically or based on culture. Additionally, gel or powder cadexomer iodine may be combined with the enhanced medical dressing with a recommended starting dose of 250-300 mg/3 $cm^2$.

The container 110 may be an air tight, sealed or selectively seal-able, and sterile container which may be made of a suitable substance such as plastic or glass, which may be unreactive to the preparation process of the enhanced medical dressing 602. In one embodiment, the container 110 itself may be used as packaging to contain the dressing 103, collagen enhancer 102, and antibiotic enhancer 104, to provide the set-up 100 to a user for allowing the user to prepare the enhanced medical dressing 602. Alternatively, the enhanced medical dressing 602 may be prepared or provided in a separate container.

Turning back to FIG. 1, the dressing 103 may be a medical gauze, polyurethane foam, hydrocolloid, or composite. In one example, the dressing 103 may be a collagen dressing. The dressing 103 may belong to a class of degradable dressings such that the dressing 103 may gradually disintegrate when brought in contact with physiological moisture of a wound (e.g. wound 604 of FIG. 6), on application of the dressing 103 onto the wound. The dressing 103 may be made of any suitable material. For example, the dressing 103 may be an absorbent, open-pored, sterile, freeze-dried matrix including collagen and oxidized regenerated cellulose (ORC). The dressing 103 may be sterilized and in a ready-to-use form. The dressing 103 may have a pad or fiber like appearance. In the illustrated embodiment of FIG. 1, the dressing 103 has a rectangular shape. In other embodiments, the dressing 103 may have a circular, square, or other suitable shape. The dressing 103 may include layers, and sizing of the dressing 103 may vary based on wound type or requirements of an application.

The collagen enhancer 102 may be a collagen powder. Alternatively, the collagen enhancer 102 may be in the form of a liquid collagen. For example, the collagen enhancer 102 may include hydrolyzed collagen sometimes referred to as collagen hydrolysate, gelatine, gelatine hydrolysate, hydrolyzed gelatine, and/or collagen peptides. In another embodiment, the collagen enhancer 102 may be a gel collagen. The collagen enhancer 102 may be a collagen including substances effective in treatment of wounds, such as flesh wounds.

For example, in presence of potential stimuli such as local tissue ischemia, bioburden, necrotic tissue, repeated trauma, etc., a wound may continue to remain in an inflammatory phase contributing to chronicity of the wound. One key component of these chronic wounds is an elevated level of matrix metalloproteinases (MMPs). At elevated levels, MMPs may degrade nonviable collagen and viable collagen. Also, fibroblasts in chronic wounds may secrete insufficient levels or amounts of tissue inhibitors of metalloproteinases (TIMPs) to control the activity of MMPs. The collagen enhancer 102 may lower elevated levels of MMPs by acting as a 'sacrificial substrate' when applied to the wound. Further, products formed from breaking down the collagen enhancer 102 after the collagen enhancer 102 contacts with the wound may be chemotactic for a variety of cell types required for the formation of granulation tissue (e.g. from healing). In addition, the collagen enhancer 102 has the ability to absorb wound exudates and maintain a moist wound environment. The collagen enhancer 102 may assist in the migration of numerous types of cells, including fibroblasts and keratinocytes, to the wound, which plays a major role in boosting tissue growth in a wound bed. The collagen enhancer 102 may be suitable for an abundance of acute and chronic wound types, for example, pressure ulcers, burns, diabetic foot ulcers, lacerations, surgical wounds, etc.

The collagen enhancer 102 is suitable for prolonged use, such as 24 hours to 10 days of use, in the management of wounds including: partial- and full-thickness wounds, pressure ulcers (stages 1-4), venous ulcers, diabetic ulcers, partial and full-thickness burns, acute wounds, abrasions, traumatic wounds healing by secondary intention, and donor sites and other surface wounds. The collagen enhancer 102 may be broken down by natural enzymes present in wound fluids to form a protective gel on the wound bed to protect from dehydration. The collagen enhancer 102 does not need to be removed from the wound and provides a moist environment which promotes rapid healing. The collagen enhancer 102 is non-toxic and non-irritating. It is to be understood that the properties, features, functions, and attributes described herein with respect to the collagen enhancer 102 may apply to collagen included in the dressing 103.

The antibiotic enhancer 104 may include any known antibiotic used to treat bacterial infections, for example linezolid that can be used for local or topical usage on specified areas of the human body. The antibiotic 104 is used to stop or inhibit growth of bacteria (e.g. bacterial biofilms) when applied on the wound. The antibiotic enhancer 104 may increase levels of certain natural substances in the human body, for example dopamine, norepinephrine, and serotonin. The antibiotic enhancer 104 may be in the form of a liquid, a gel, or a powder. Based on the requirements, a quantity and strength of the antibiotic enhancer 104 provided in the kit 100 may vary.

It is to be understood that any appropriate substance or composition that inhibits biofilm formation or quorum sensing may be included as an appropriate enhancer 106.

The enhanced medical dressing 602 may be prepared immediately before being applied to the wound. In some examples, the enhanced medical dressing 602 may be prepared a few minutes or hours prior to application on the wound. In order to prepare the enhanced medical dressing 602, the dressing 103 and enhancers 106 may be placed all at once or one after another into the container 110. In one embodiment, first the enhancers 106 may be placed within the container 110 and after a time period, the dressing 103 may be added into the container 110. The collagen enhancer 102 may be added before the antibiotic enhancer 104. In another example, the antibiotic enhancer 104 may be added before the collagen enhancer 102.

Based on a form and packaging of the enhancers 106, the enhancers 106 may be poured into the container 110 directly or with the help of a spatula, spoon, or other sterile mixing element. The dimensions of the container 110 are so chosen that all the substances required to form the enhanced medical dressing 602 can be easily received into the container 110. The procedure of preparing the enhanced medical dressing 602 will now be explained in detail in connection with FIGS. 2-5.

Figure 2:
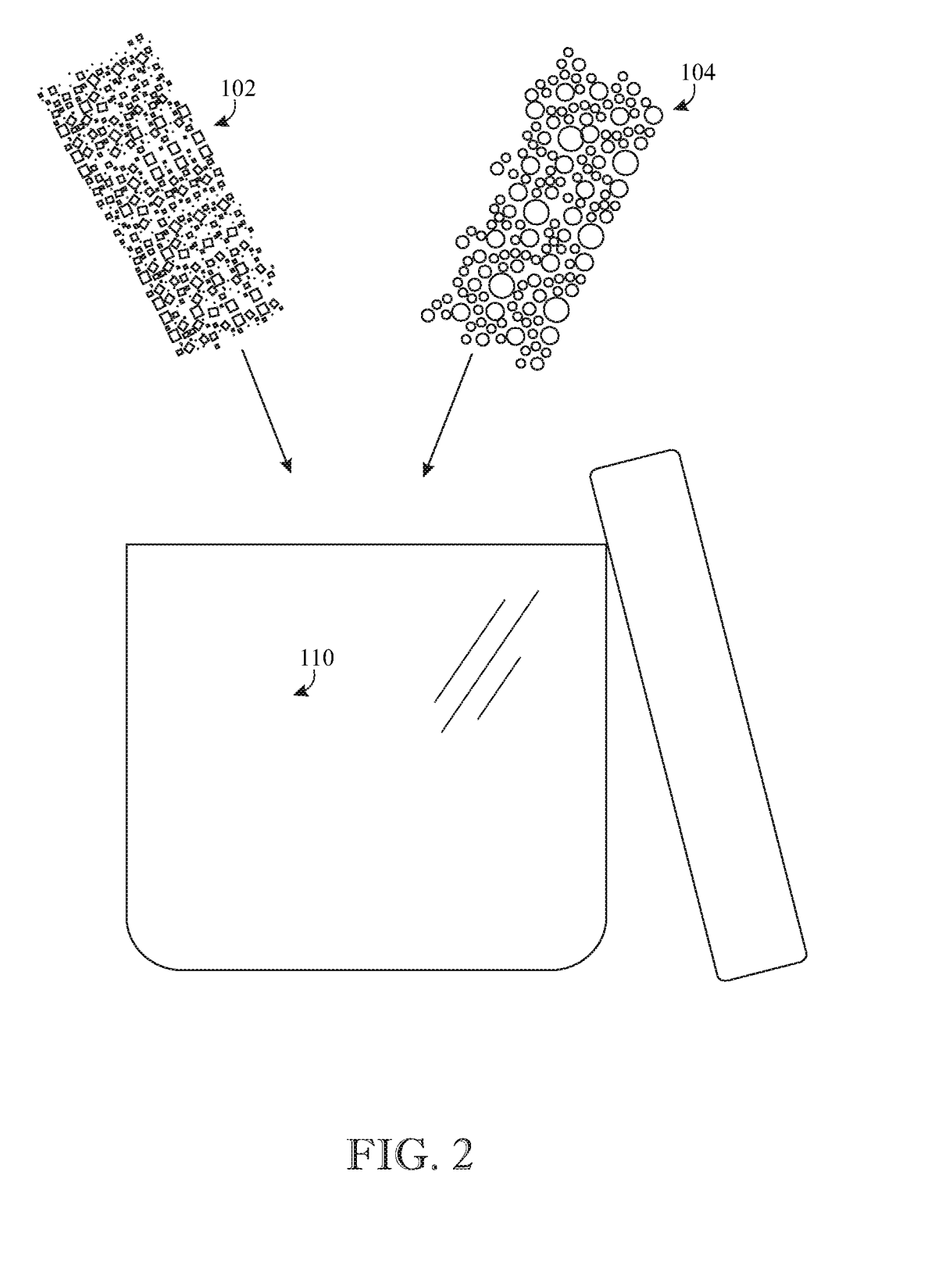
FIG. 2 presents a schematic view of enhancers being placed in the container, in accordance with aspects of the present disclosure.

Referring to FIG. 2, the enhancers 106 are introduced into the container 110. The proportion of the collagen enhancer 102 and antibiotic enhancer 104 may be predetermined based on type and size of a wound. In one example, the enhancers 106 are simultaneously introduced into the container 110. In another example, first the collagen enhancer 102 is introduced into the container 110 and then the antibiotic enhancer 104 is added to the container 110. In yet another example, the antibiotic enhancer 104 is initially placed into the container 110 and subsequently the collagen enhancer 102 is added into the container 110.

Figure 3:
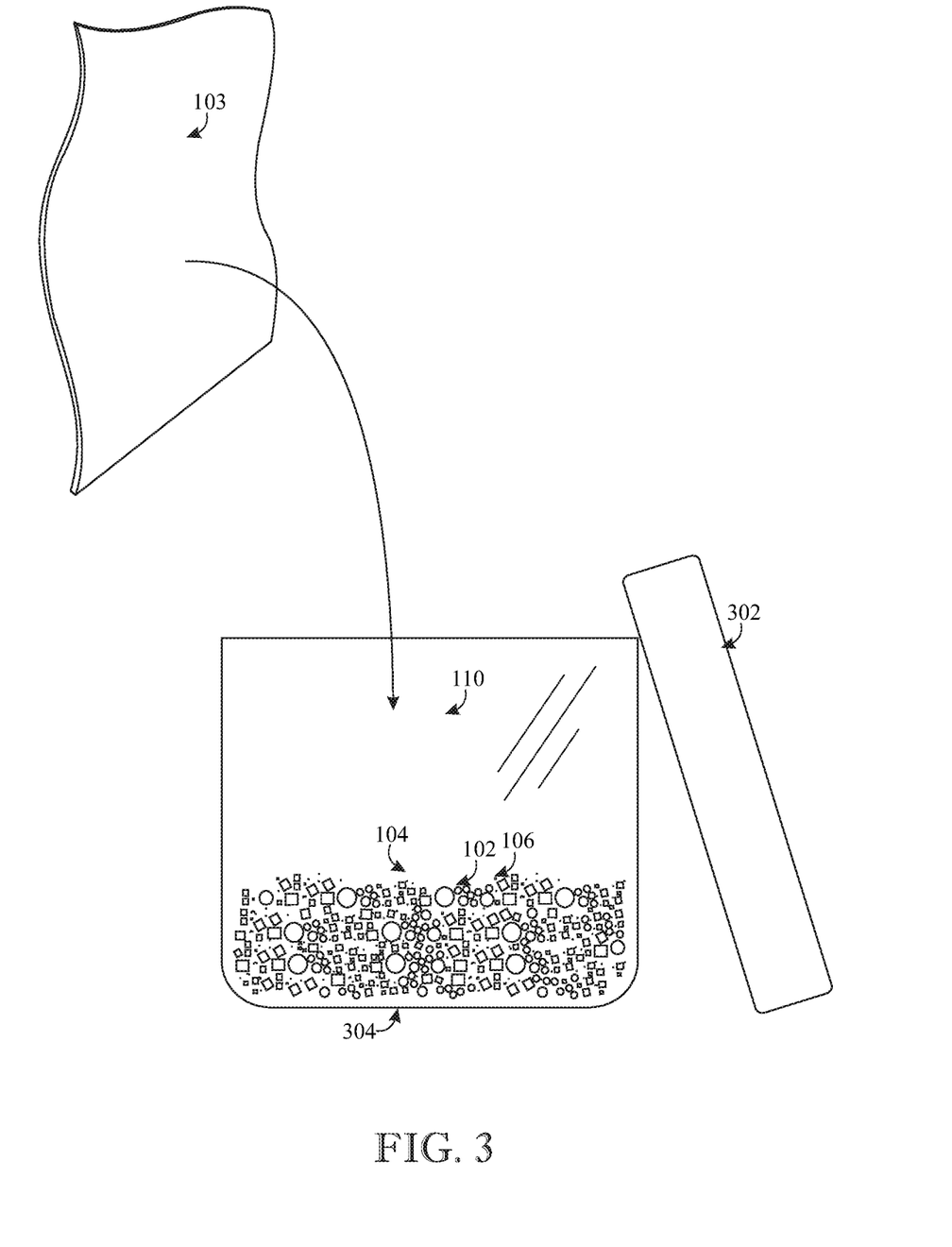
FIG. 3 presents a schematic view of a dressing material being placed into the container, in accordance with aspects of the present disclosure.

Referring to FIG. 3, the container 110 includes a lid 302 or a cover that is removably attached to the container 110. If not already open, the lid 302 may be detached from the container 110 and placed at a side of the container 110 to expose a free open end of the container 110. Further, the packaging of each of the enhancers 106 may be opened, and an open end of the packaging containing the enhancers 106 respectively may be brought proximate to an open top end of the container 110, such that the contents of the packaging including the enhancers 106 respectively may be freely dropped down into the container 110 by the force of gravity. In one embodiment, the packaging may need to be squeezed to empty the enhancers 106 into the container 110. In another embodiment, a sterile element such as, a spoon may be used to force the respective enhancers 106 to fall into the container 110.

The enhancers 106 may collect and intermix with each other on a bottom surface 304 of the container 110. Further, the dressing 103 may be placed into the container 110 such that the dressing may amass or absorb the enhancers 106 thereon. As such, the one or more enhancers 106 may augment the dressing 103. In one embodiment, the dressing 103 may be added to the container 110 such that a maximum surface area of the dressing 103 may come in contact with the enhancers 106 present within the container 110. The dressing 103 may be introduced downwards as shown in FIG. 5, engaging the interior bottom surface 304 of the container 110 such that the dressing 103 is brought in contact with intermixed enhancers 106.

In some embodiments, the dressing 103 may be fragmented or provided in a number of smaller pieces to increase the surface area of the dressing 103 exposable to the enhancers 106. For example, the dressing may be fragmented such that the enhanced medical dressing, being fragmented, may be sprinkled onto the wound.

Figure 4:
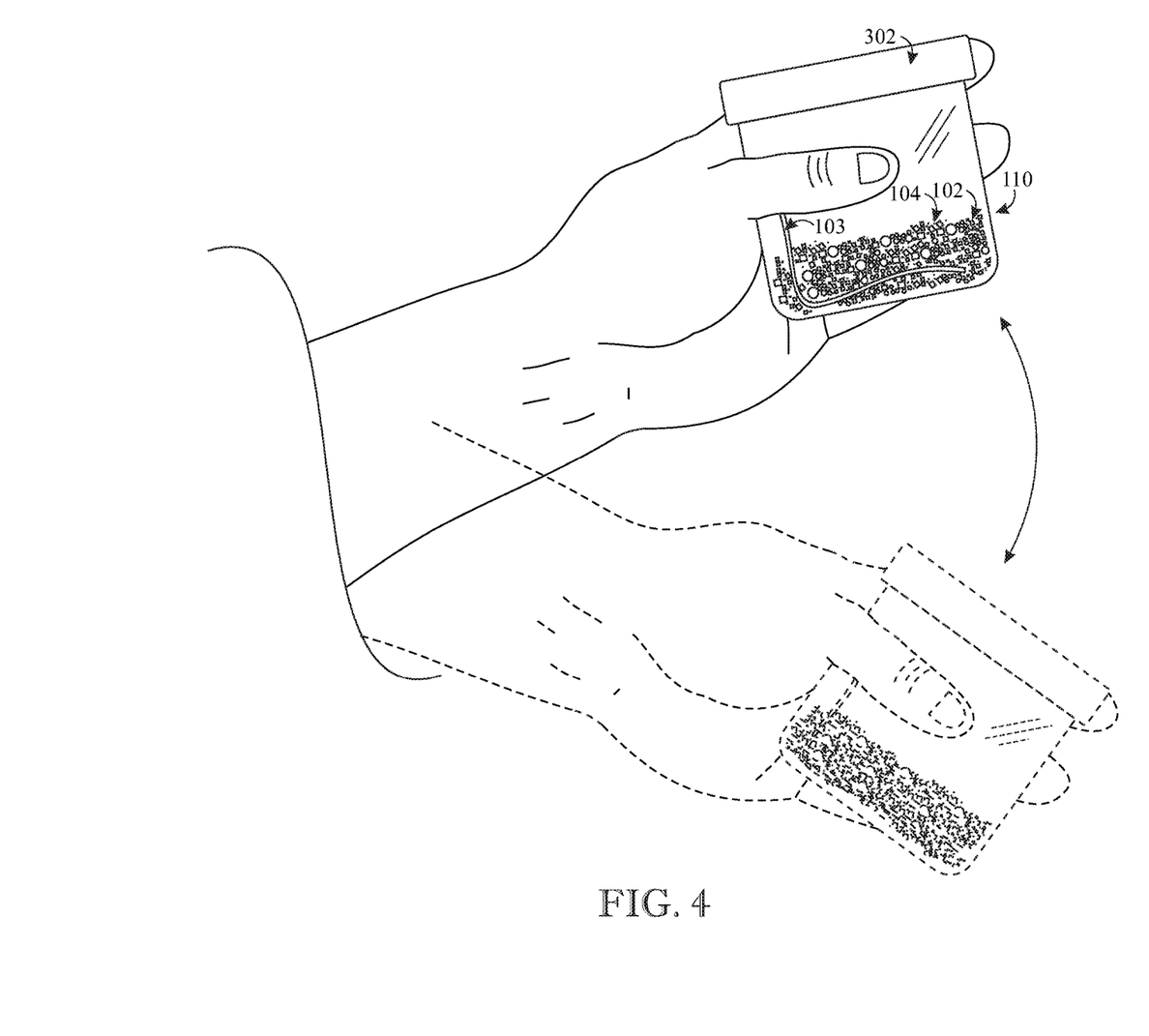
FIG. 4 presents a schematic view of elements being mixed for preparing the enhanced medical dressing, in accordance with aspects of the present disclosure.

Referring to FIG. 4, further preparing the enhanced medical dressing 602 is illustrated. After the substances (dressing 103 and enhancers 106) of the enhanced medical dressing 602 are placed into the container 110, certain additional steps may need to be performed to improve augmenting the dressing 103 with the enhancers 106. Accordingly, the lid 302 of the container 110 may be restored onto the container 110. Further, mixing the enhancers 106 with the dressing 103 may be improved by mechanically shaking the container 110, to intermix the contents of the container 110. For example, the enhancers 106 may attach to the dressing 103 inside the container 110. Alternatively, the contents of the container 110 may be intermixed using a swirling or circular type motion. An apparatus may also be used to mix the contents of the container 110, such as a sterile spoon or spatula. A number of times and or duration of shaking the container 110 may vary based on specific requirements of the application.

Figure 5:
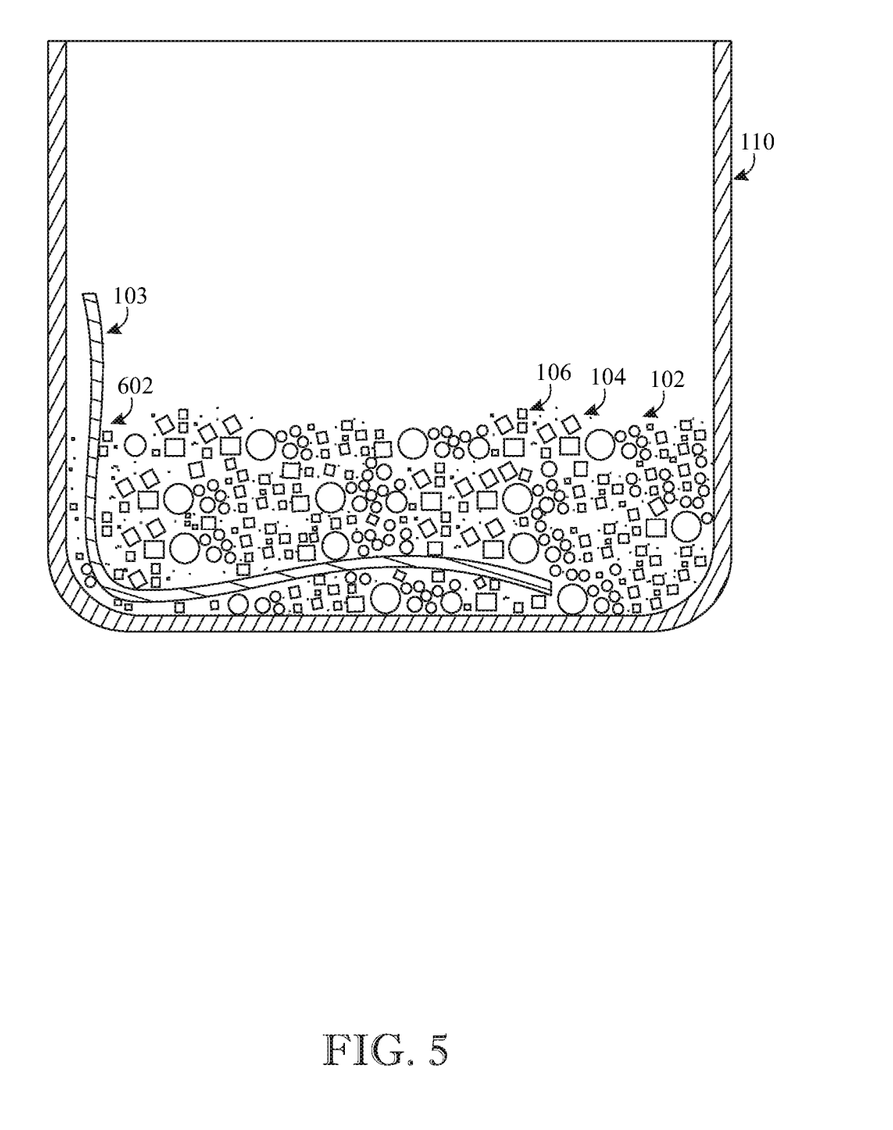
FIG. 5 presents a schematic view of the dressing being augmented with enhancers, in accordance with aspects of the present disclosure.

Referring to FIG. 5, after the mixing action is performed, the contents of the container 110 may be allowed to sit for a specified time period. The enhancers 106 attach or adhere to the dressing 103. The attachment of the enhancers to the dressing may be caused by the enhancers 106 adhering to the top and/or bottom surfaces of the dressing 103. The enhancers 106 may adhere to the dressing 103 due to material properties of any one or both of the enhancers 106, and/or that of the dressing 103. In one example, electrostatic force (e.g. caused by mixing) or Van der Waals forces between the enhancers 106 and the dressing may cause the enhancers 106 to attach to the dressing 103, forming the enhanced medical dressing 602 (see FIG. 6). The enhancers 106 attach to the top and bottom surfaces of the dressing 103. Augmenting the dressing 103 may take place such that the enhancers 106 may be evenly distributed on the top and/or bottom surfaces of the dressing 103. Referring to FIG. 6, after preparing the dressing 103, the enhanced medical dressing 602 can be applied to the wound 604 for treating the wound 604. For example, the enhanced medical dressing 602 can be applied to flesh wounds, such as lesions and cuts.

In other embodiments, the enhanced medical dressing 602 may additionally or optionally include micronutrients, such as vitamins (example: C, D, zinc). Further, the enhanced medical dressing 602 may include indocyanine green (ICG) for topical use with near-infra-red fluorescent vascular imaging devices to assist with vascular and/or lymph-node mapping and cancer surgery. The recommended starting dose of ICG is 2.5 mg/3 cm$^2$. These substances may be added to the container 110 while preparing the dressing 103. Alternatively, these substances may be present on the dressing 103 or in one or more of the enhancers 106.

In cases of inadequate nutrition, ischemia, and radiation injury, micronutrient therapy may be of help to the chronic wound which has not responded to standard therapies. Vitamin C is essential as an antioxidant and critical in collagen synthesis. Vitamin C may be added to the enhanced wound dressing with a recommended starting dose of 6 mg/3 cm$^2$. Zinc is an important cofactor in collagen synthesis, and may be added to the enhanced wound dressing with a recommended starting dose of 2 mg/3 cm$^2$ Vitamin D is a pleiotropic steroid hormone with known anti-inflammatory, pro-differentiation, immunomodulatory, and antibacterial properties. While most likely to support wound healing in known cases of deficiency, it may also be important in certain acute and chronic wounds. The dose of vitamin D may be 40 IU/3 cm$^2$ based on a 400 IU/28 cm$^2$ dressing. Such recommended dosing may be based on a dressing (e.g. Prisma) of 28 cm$^2$ and an appropriate thickness, with 60 mg Vitamin C and 15 mg Zinc.

The enhanced medical dressing 602 may be removed from the container 110 and applied on the wound 604 (FIG. 6). The enhanced medical dressing 602 may be removed using sterilized fingers or any other grasping tool such that the enhanced medical dressing 602 is gently removed from the container 110 without damaging the enhanced medical dressing 602. The prepared enhanced medical dressing 602 includes the enhancers 106 augmented thereon. The top and/or bottom surface of the enhanced medical dressing 602 is brought in contact with the wound by placing the enhanced medical dressing 602 face down such that an augmented surface is bought in direct contact with the wound 604. Prior to the application of the enhanced medical dressing 602, the wound 604 may be cleaned using a suitable sterile solution. In FIG. 6, the exemplary wound 604 is on a forearm of the patient, and in FIG. 10, a wound 1002 is on a foot of a patient. Clothing may be pushed back to expose the wound 604 for easy application of the enhanced medical dressing 602.

Figure 7:
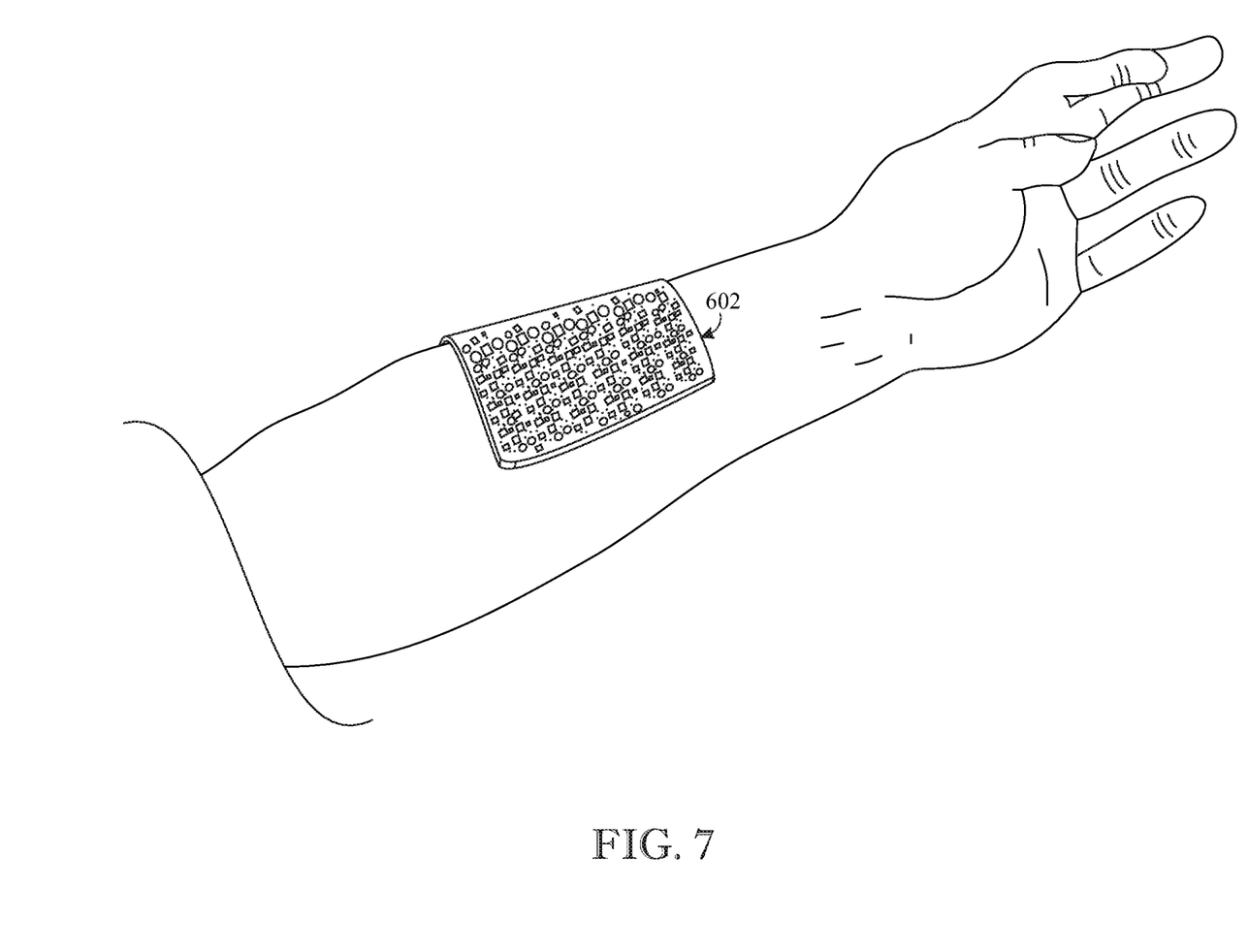
FIG. 7 presents a perspective view of the enhanced medical dressing applied onto the wound, in accordance with aspects of the present disclosure.
Figure 8:
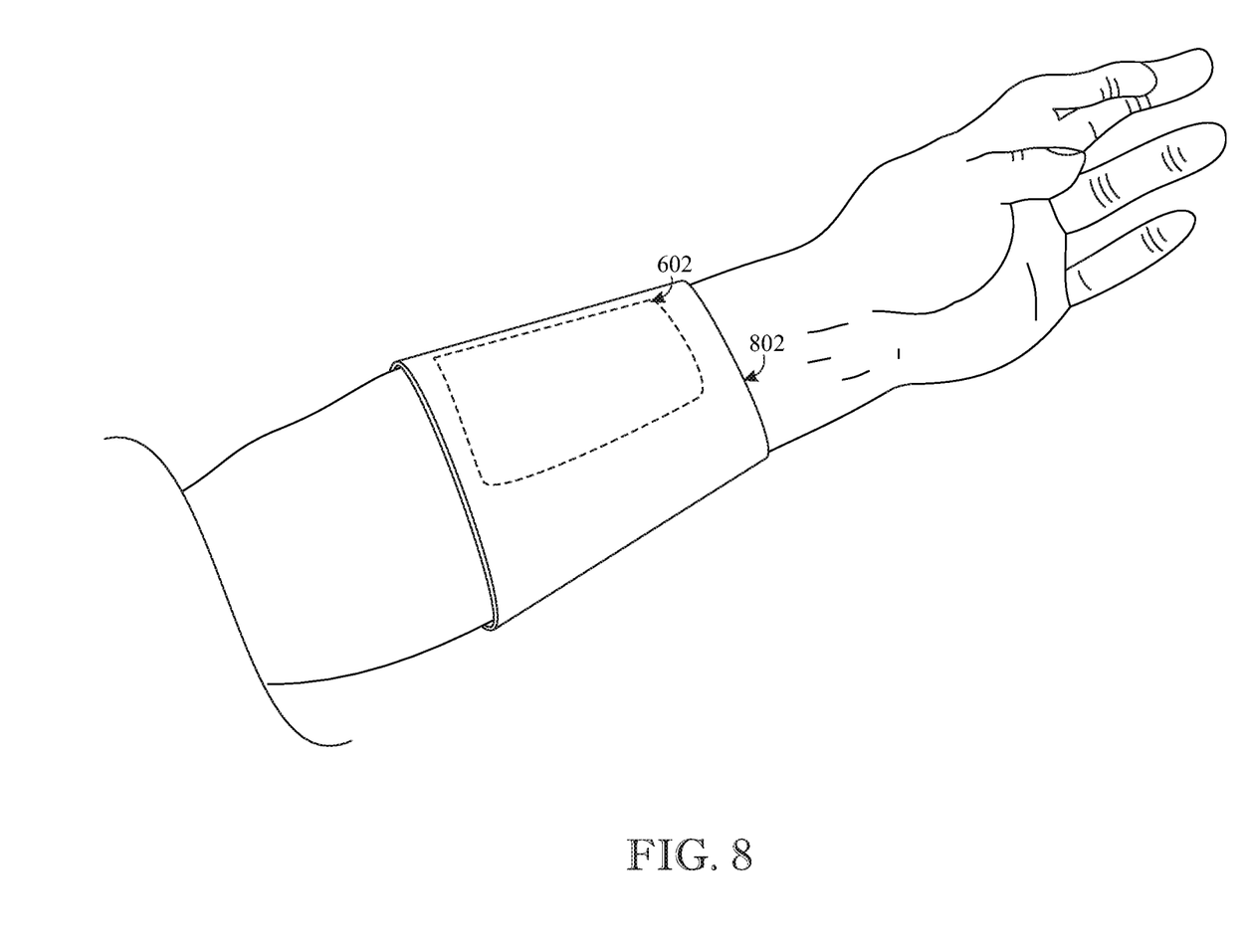
FIG. 8 presents a perspective view of the enhanced medical dressing bandaged to an arm while covering the wound, in accordance with aspects of the present disclosure.

Referring to FIG. 7, the enhanced medical dressing 602 is applied onto the wound 604. The enhanced medical dressing 602 is placed such that the wound 604 is completely concealed by the enhanced medical dressing 602. Further, as shown in FIG. 8, a bandage 802 may be placed in surrounding contact with the enhanced medical dressing 602 to hold the enhanced medical dressing 602 in place over the wound 604. The enhanced medical dressing may also be placed at the base of the wound and covered by negative pressure wound therapy application. The bandage 802 is made of any suitable breathable material known in the art.

Figure 9:
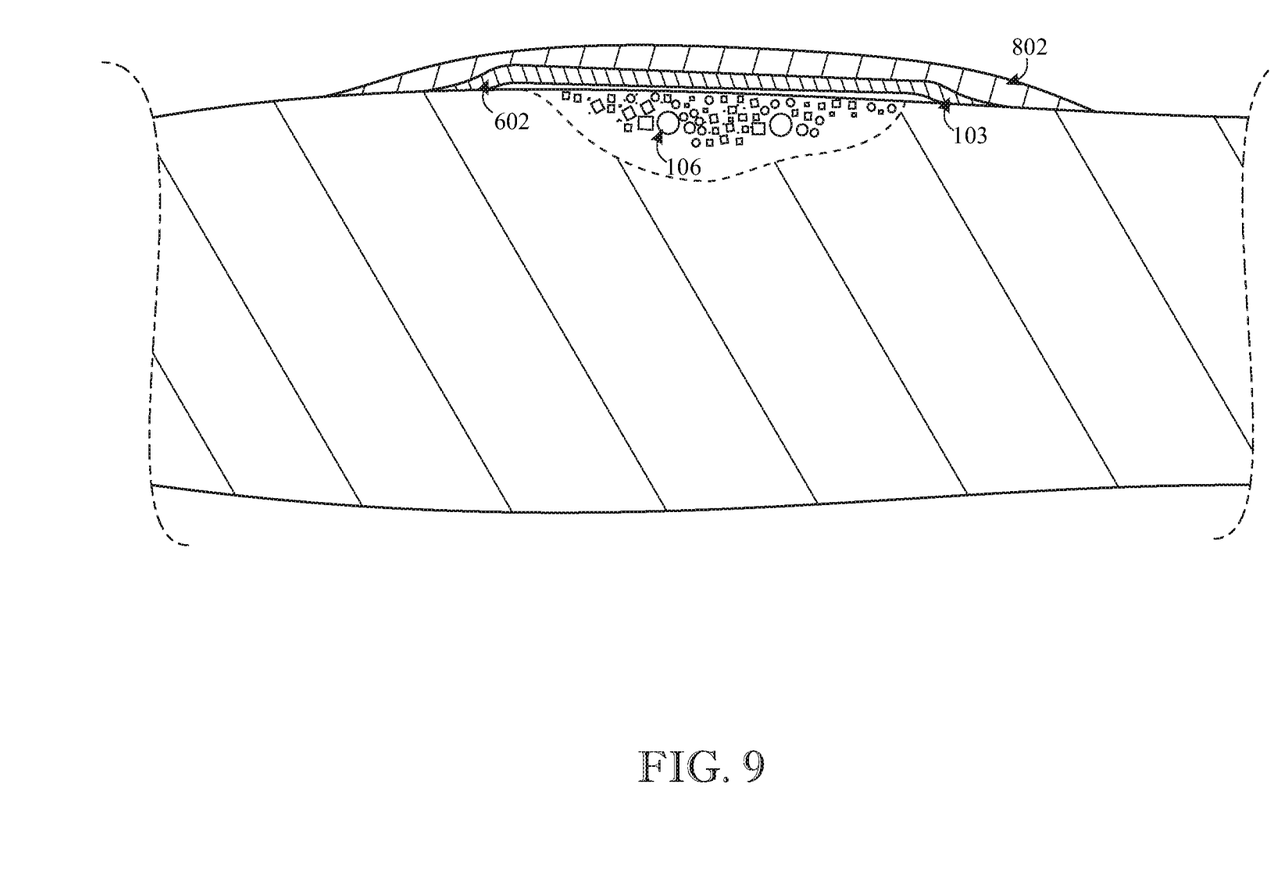
FIG. 9 presents a sectional side elevation view of the enhanced medical dressing contacting the wound, in accordance with aspects of the present disclosure.

FIG. 9 shows a healing action of the enhanced medical dressing 602 when applied on the wound 604. On exposure to the wound 604, the enhancers 106 on the enhanced medical dressing 602 are released into the wound 604. More specifically, the enhancers 106 are transferred from the top and/or bottom surfaces of the enhanced medical dressing 602 into the wound for treating the wound 604. In some cases, the enhanced medical dressing 602 may gradually disintegrate on contact with physiological moisture in the wound 604. Further, the enhancers 106 may slowly dissipate into the wound 604 (e.g. via a timed-release configuration). For example, collagen enhancer 102 may be configured to be released first, then antibiotic enhancer 104 may be configured to be released second, or vice-versa. The frequency of re-application of the enhanced medical dressing 602 onto the wound 604 may vary based on a severity of the wound 604. Further, the bandage 802 may need to be changed based on the disintegration of the enhanced medical dressing 602.

The enhancers 106 may be released in response to being exposed to moisture (e.g. drainage) of the wound 604. For example, an electrostatic force may cause the one or more enhancers 106 to attach to the dressing 103, and moisture being applied to the enhanced dressing 602 may cause such an electrostatic force to be reduced or eliminated enough to cause the enhancers 106 to propagate into the wound 604. More drainage of the wound may result in a greater volume of enhancers 106 being released into the wound 604.

Figure 10:
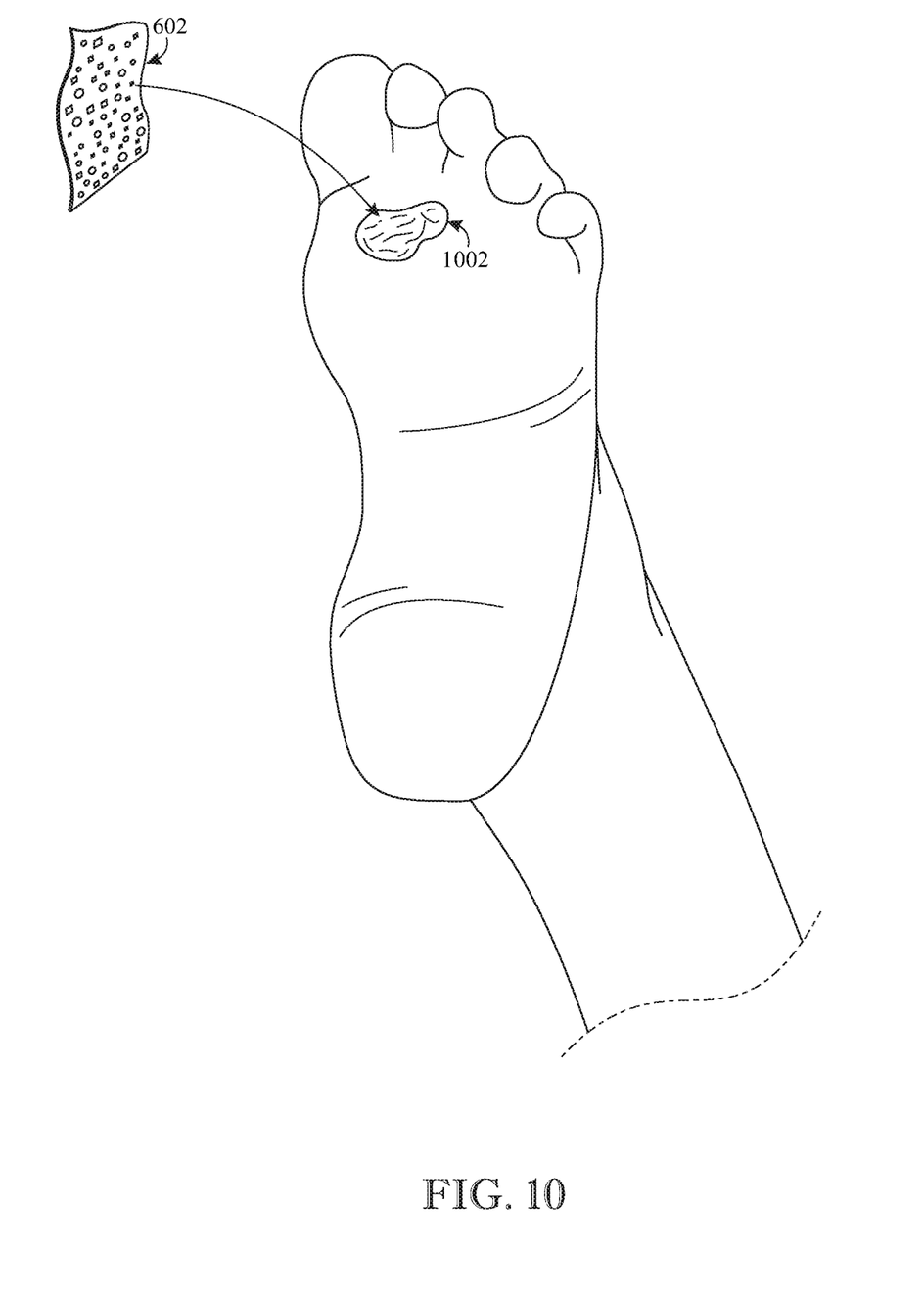
FIG. 10 presents a perspective view of another application of the enhanced medical dressing for a foot specific wound, in accordance with aspects of the present disclosure.
Figure 11:
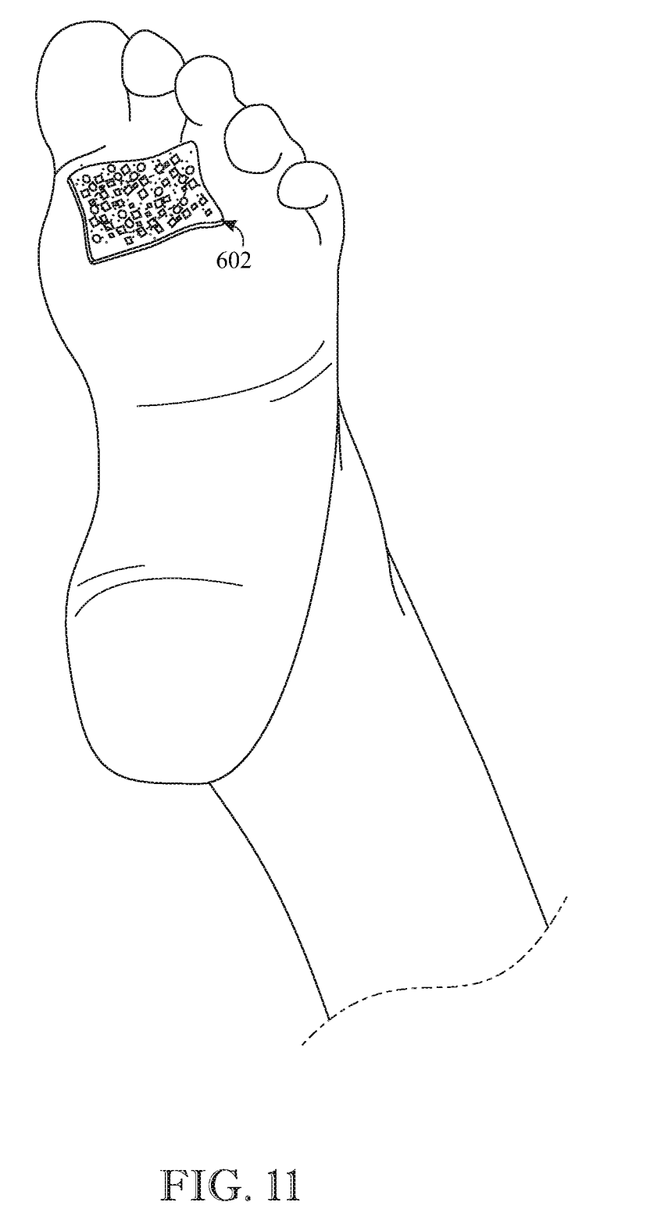
FIG. 11 presents a perspective view of the enhanced medical dressing applied onto the foot specific wound of FIG. 10, in accordance with aspects of the present disclosure.

FIGS. 10 and 11 illustrate another application of the enhanced medical dressing 602 on a foot wound 1002. As shown, the foot wound 1002 may be present on a sole of a foot of the patient. As described above, the dressing 103 may be prepared and applied onto the wound 1002 such that the wound 1002 is completely concealed by the enhanced medical dressing 602 which has the enhancers 106 attached thereon.

The enhanced medical dressing 602 allows for immediate delivery of antimicrobial substance to ischemic wound tissue and delivers needed nutrients (e.g. collagen) and antibiotics to the wound. Moreover, the enhanced medical dressing 602 can be easily applied to the wound 604 or 1002 without requiring intravenous or oral administration of the enhancers 106. Although the enhanced medical dressing 602 is primarily used for wound care, there are multiple other applications that are possible for the enhanced medical dressing 602, for example post-operative complications where bacterial biofilm has caused dehiscence and/or exposed orthopedic hardware.

It is to be understood that although the herein disclosed enhanced medical dressing may be prepared on-site at will, the enhanced medical dressing may be pre-prepared in a factory or at a manufacturer and sold or provided pre-packaged. For example, the enhanced medical dressing 602 may be sold or provided in an air-tight and sterile package, having already been prepared as described above.

In conclusion, disclosed is a method of preparing an enhanced medical dressing for treating a wound, the method comprising, augmenting a dressing with an enhancer to form an enhanced dressing. The dressing may be an enhanced medical dressing for treating flesh wounds. The enhancer may be a composition including at least one of collagen and an antibiotic. The collagen may be a collagen powder and the antibiotic may be linezolid. The antibiotic may be in form of a powder. The collagen may be in form of a liquid. The collagen may be in form of a gel. The antibiotic may be in form of a liquid. The antibiotic may be in form of a gel. In the augmenting step, at least one of the dressing and the enhancer may be configured to cause the dressing and the enhancer to adhere to one another. The dressing and the enhancer may be configured to adhere to one another via electrostatic force. The augmenting step may include mixing the dressing and the enhancer in a container. The dressing may be configured to degrade in contact with physiological moisture. The dressing may be a collagen dressing including oxidized regenerated cellulose and collagen. At least one of the collagen and antibiotic may be configured to be released into a wound contacting the enhanced dressing. The method further comprises, fragmenting the dressing to increase a surface area of the dressing. The dressing and the enhancer may be provided in a kit. The method further comprises, applying the enhanced dressing to a wound.

Furthermore, disclosed is an apparatus for treating a wound, the apparatus comprising, a material (e.g. dressing) including collagen and an antibiotic, the material configured to degrade in contact with physiological moisture to release collagen and the antibiotic from the material. The material may be fragmented to increase an exposed surface area of the material.

Also disclosed is a system for treating a wound, the system comprising, a material including collagen, a collagen enhancer, and an antibiotic enhancer, wherein the material, the collagen enhancer, and the antibiotic enhancer, may be configured to attach to one another upon being mixed together in a container. The material may be an absorbent, open-pored, sterile, matrix including collagen and oxidized regenerated cellulose.

As such, the enhanced medical dressing may promote the disruption and/or inhibition of biofilm formation in a wound and promote healing more effectively than conventional wound dressing methods and treatments. The collagen enhancer 102 may modulate the white blood cell response in such a way as to decrease wound area inflammation. Introducing collagen and an antibiotic such as linezolid into a wound provides a synergistic effect, where the collagen promotes the more rapid attachment of the antibiotic to wound area bacteria. Similarly, the enhanced dressing promotes more rapid uptake of the antibiotic into the wound area biofilm, drawing the bacteria away from a protected state (e.g. biofilm), or from otherwise untreatable regions of the skin. Thus, by multiple mechanisms, the antibiotic therapy is more rapidly bacteriostatic and/or bacteriocidal. Further, by application of the antibiotic to the wound area, the systemic antibiotic course, if elected, may be reduced.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A method of preparing an enhanced medical dressing for treating a wound, the method comprising:
   augmenting a dressing with an enhancer to form an enhanced dressing;
   wherein the enhancer is a composition including at least one of collagen and an antibiotic;
   wherein augmenting the dressing includes placing the dressing in a container with the enhancer and mechanically displacing the container to coat the dressing with the enhancer;
   wherein placing the dressing in the container with the enhancer is done after the dressing has been manufactured and has been provided to a user in an non-augmented state, to allow the user to augment the dressing at will;
   wherein placing the dressing in the container with the enhancer is done on-site where a wound is to be treated, such that a user is able to select a suitable type and dosage of the enhancer;
   wherein after being coated by the enhancer, the enhanced dressing is placed on the wound to allow the enhancer to be released from the enhanced dressing into the wound; and
   wherein moisture from the wound is allowed to penetrate the enhanced dressing to cause the enhancer to be released into the wound.

2. The method of claim 1, wherein if the enhancer includes collagen, the collagen is a collagen powder, and if the enhancer includes an antibiotic, the antibiotic is linezolid.

3. The method of claim 1, wherein the antibiotic is in the form of a powder.

4. The method of claim 1, wherein the collagen is in the form of a liquid.

5. The method of claim 1, wherein the collagen is in the form of a gel.

6. The method of claim 1, wherein the antibiotic is in the form of a liquid.

7. The method of claim 1, wherein the antibiotic is in the form of a gel.

8. The method of claim 1, wherein displacing the container includes shaking the container, and shaking the container causes the enhancer to contact the dressing within the container to cause the enhancer to coat the dressing within the container via van der Waals forces between the dressing and the enhancer.

9. The method of claim 1, wherein displacing the container includes shaking the container, and shaking the container generates electrostatic forces between the dressing and the enhancer to cause the enhancer to adhere to the dressing within the container.

10. The method of claim 1, wherein the dressing is a collagen dressing that degrades in contact with physiological moisture.

11. The method of claim 1, wherein the dressing is a collagen dressing including oxidized regenerated cellulose and collagen.

12. The method of claim 1, wherein the method further comprises, fragmenting the dressing to increase a surface area of the dressing.

13. The method of claim 1, wherein the dressing and the enhancer are provided in a kit.

\* \* \* \* \*